United States Patent
Baril et al.

(10) Patent No.: US 11,426,203 B2
(45) Date of Patent: Aug. 30, 2022

(54) TISSUE GUARDS AND SYSTEMS INCORPORATING THE SAME FOR TISSUE SPECIMEN REMOVAL PROCEDURES AND OTHER SURGICAL PROCEDURES

(71) Applicant: Covidien LP, Mansfield, MA (US)

(72) Inventors: Jacob C. Baril, Norwalk, CT (US); Saumya Banerjee, Hamden, CT (US); Christopher M. Meehan, New Haven, CT (US); George S. Matta, Plainville, MA (US); Amy L. Kung, Hamden, CT (US); Scott J. Prior, Shelton, CT (US); Matthew A. Dinino, Newington, CT (US)

(73) Assignee: Covidien LP, Mansfield, MA (US)

( * ) Notice: Subject to any disclaimer, the term of this patent is extended or adjusted under 35 U.S.C. 154(b) by 182 days.

(21) Appl. No.: 16/879,691

(22) Filed: May 20, 2020

(65) Prior Publication Data

US 2020/0367932 A1 Nov. 26, 2020

Related U.S. Application Data

(60) Provisional application No. 62/852,223, filed on May 23, 2019.

(51) Int. Cl.
*A61B 17/34* (2006.01)
*A61B 90/00* (2016.01)

(52) U.S. Cl.
CPC ...... *A61B 17/3494* (2013.01); *A61B 17/3423* (2013.01); *A61B 2090/036* (2016.02); *A61B 2217/005* (2013.01)

(58) Field of Classification Search
CPC ............ A61B 17/3424; A61B 17/3494; A61B 2090/036; A61B 2017/3425;
(Continued)

(56) References Cited

U.S. PATENT DOCUMENTS

| | | |
|---|---|---|
| 5,643,283 A | 7/1997 | Younker |
| 5,941,873 A | 8/1999 | Korenfeld |

(Continued)

FOREIGN PATENT DOCUMENTS

| | | |
|---|---|---|
| EP | 2226023 A1 | 9/2010 |
| WO | 2004002334 A1 | 1/2004 |
| WO | 2014158880 A1 | 10/2014 |

OTHER PUBLICATIONS

Extended European Search Report issued in corresponding European Application No. 20175900.8 dated Sep. 18, 2020, 8 pages.

*Primary Examiner* — Tan-Uyen T Ho
*Assistant Examiner* — Bridget E. Rabaglia
(74) *Attorney, Agent, or Firm* — Carter, DeLuca & Farrell LLP

(57) ABSTRACT

A tissue guard includes a body defining an open proximal end, an open distal end, and a lumen extending through the body between the open proximal end and the open distal end. The tissue guard further includes a lip extending radially outwardly from the open proximal end of the body. The lip includes a plurality of spaced-apart cut-outs defined about the outer circumference of the lip to define a plurality of tabs of the lip. Each tab includes an outer edge segment. The body and the lip are monolithically formed as a single piece of material.

18 Claims, 7 Drawing Sheets

(58) Field of Classification Search
CPC ...... A61B 2017/3427; A61B 2218/008; A61B
90/04; A61B 2090/0427; A61B 17/3431;
A61B 17/3429; A61M 39/02; A61M
2039/0226
USPC ............. 606/172; 600/205, 208; 604/164.09,
604/208.01, 288.01, 208.02
See application file for complete search history.

(56) References Cited

U.S. PATENT DOCUMENTS

| | | | |
|---|---|---|---|
| 6,059,793 A | 5/2000 | Pagedas | |
| 6,156,055 A | 12/2000 | Ravenscroft | |
| 6,162,209 A | 12/2000 | Gobron et al. | |
| 6,171,317 B1 | 1/2001 | Jackson et al. | |
| 6,206,889 B1 | 3/2001 | Bennardo | |
| 6,224,612 B1 | 5/2001 | Bates et al. | |
| 6,228,095 B1 | 5/2001 | Dennis | |
| 6,248,113 B1 | 6/2001 | Fina | |
| 6,258,102 B1 | 7/2001 | Pagedas | |
| 6,264,663 B1 | 7/2001 | Cano | |
| 6,270,505 B1 | 8/2001 | Yoshida et al. | |
| 6,280,451 B1 | 8/2001 | Bates et al. | |
| 6,344,026 B1 | 2/2002 | Burbank et al. | |
| 6,350,266 B1 | 2/2002 | White et al. | |
| 6,350,267 B1 | 2/2002 | Stefanchik | |
| 6,358,198 B1 | 3/2002 | Levin et al. | |
| 6,368,328 B1 | 4/2002 | Chu et al. | |
| 6,383,195 B1 | 5/2002 | Richard | |
| 6,383,197 B1 | 5/2002 | Conlon et al. | |
| 6,387,102 B2 | 5/2002 | Pagedas | |
| 6,406,440 B1 | 6/2002 | Stefanchik | |
| 6,409,733 B1 | 6/2002 | Conlon et al. | |
| 6,447,523 B1 | 9/2002 | Middleman et al. | |
| 6,530,923 B1 | 3/2003 | Dubrul et al. | |
| 6,537,273 B1 | 3/2003 | Sosiak et al. | |
| 6,752,822 B2 | 6/2004 | Jespersen | |
| 6,805,699 B2 | 10/2004 | Shimm | |
| 6,951,533 B2 | 10/2005 | Foley | |
| 6,986,774 B2 | 1/2006 | Middleman et al. | |
| 7,037,275 B1 | 5/2006 | Marshall et al. | |
| 7,052,501 B2 | 5/2006 | McGuckin, Jr. | |
| 7,087,062 B2 | 8/2006 | Dhindsa | |
| 7,101,379 B2 | 9/2006 | Gregory, Jr. et al. | |
| 7,101,380 B2 | 9/2006 | Khachin et al. | |
| 7,112,172 B2 | 9/2006 | Orban, III et al. | |
| 7,115,125 B2 | 10/2006 | Nakao et al. | |
| 7,144,400 B2 | 12/2006 | Byrum et al. | |
| 7,169,154 B1 | 1/2007 | Que et al. | |
| 7,229,418 B2 | 6/2007 | Burbank et al. | |
| 7,285,126 B2 | 10/2007 | Sepetka et al. | |
| 7,316,692 B2 | 1/2008 | Huffmaster | |
| 7,357,801 B2 | 4/2008 | Burbank et al. | |
| 7,534,252 B2 | 5/2009 | Sepetka et al. | |
| 7,547,310 B2 | 6/2009 | Whitfield | |
| 7,615,013 B2 | 11/2009 | Clifford et al. | |
| 7,618,437 B2 | 11/2009 | Nakao | |
| 7,645,283 B2 | 1/2010 | Reynolds et al. | |
| 7,670,346 B2 | 3/2010 | Whitfield | |
| 7,678,118 B2 | 3/2010 | Bates et al. | |
| 7,722,626 B2 | 5/2010 | Middleman et al. | |
| 7,727,227 B2 | 6/2010 | Teague et al. | |
| 7,731,722 B2 | 6/2010 | Lavelle et al. | |
| 7,731,723 B2 | 6/2010 | Kear et al. | |
| 7,762,959 B2 | 7/2010 | Bilsbury | |
| 7,762,960 B2 | 7/2010 | Timberlake et al. | |
| 7,875,038 B2 | 1/2011 | Que et al. | |
| 7,892,242 B2 | 2/2011 | Goldstein | |
| 7,901,353 B2 | 3/2011 | Vayser et al. | |
| 7,914,540 B2 | 3/2011 | Schwartz et al. | |
| 7,918,860 B2 | 4/2011 | Leslie et al. | |
| 7,955,292 B2 | 6/2011 | Leroy et al. | |
| 8,057,485 B2 | 11/2011 | Hollis et al. | |
| 8,075,567 B2 | 12/2011 | Taylor et al. | |
| 8,118,816 B2 | 2/2012 | Teague | |
| 8,152,820 B2 | 4/2012 | Mohamed et al. | |
| 8,172,772 B2 | 5/2012 | Zwolinsk et al. | |
| 8,211,115 B2 | 7/2012 | Cheng et al. | |
| 8,282,572 B2 | 10/2012 | Bilsbury | |
| 8,337,510 B2 | 12/2012 | Rieber et al. | |
| 8,348,827 B2 | 1/2013 | Zwolinski | |
| 8,409,216 B2 | 4/2013 | Parihar et al. | |
| 8,414,596 B2 | 4/2013 | Parihar et al. | |
| 8,419,749 B2 | 4/2013 | Shelton, IV et al. | |
| 8,425,533 B2 | 4/2013 | Parihar et al. | |
| 8,430,826 B2 | 4/2013 | Uznanski et al. | |
| 8,435,237 B2 | 5/2013 | Bahney | |
| 8,444,655 B2 | 5/2013 | Parihar et al. | |
| 8,486,087 B2 | 7/2013 | Fleming | |
| 8,512,351 B2 | 8/2013 | Teague | |
| 8,579,914 B2 | 11/2013 | Menn et al. | |
| 8,585,712 B2 | 11/2013 | O'Prey et al. | |
| 8,591,521 B2 | 11/2013 | Cherry et al. | |
| 8,652,147 B2 | 2/2014 | Hart | |
| 8,721,658 B2 | 5/2014 | Kahle et al. | |
| 8,734,464 B2 | 5/2014 | Grover et al. | |
| 8,777,961 B2 | 7/2014 | Cabrera et al. | |
| 8,795,291 B2 | 8/2014 | Davis et al. | |
| 8,821,377 B2 | 9/2014 | Collins | |
| 8,827,968 B2 | 9/2014 | Taylor et al. | |
| 8,870,894 B2 | 10/2014 | Taylor et al. | |
| 8,906,035 B2 | 12/2014 | Zwolinski et al. | |
| 8,956,370 B2 | 2/2015 | Taylor et al. | |
| 8,961,407 B2 * | 2/2015 | Piskun ............... | A61B 17/3462 600/204 |
| 8,968,191 B2 * | 3/2015 | Pribanic ............. | A61B 17/3423 600/208 |
| 8,968,329 B2 | 3/2015 | Cabrera | |
| 8,986,321 B2 | 3/2015 | Parihar et al. | |
| 9,005,215 B2 | 4/2015 | Grover et al. | |
| 9,017,328 B2 | 4/2015 | Bahney | |
| 9,017,340 B2 | 4/2015 | Davis | |
| 9,033,995 B2 | 5/2015 | Taylor et al. | |
| 9,084,588 B2 | 7/2015 | Farascioni | |
| 9,101,342 B2 | 8/2015 | Saleh | |
| 9,113,848 B2 | 8/2015 | Fleming et al. | |
| 9,113,849 B2 | 8/2015 | Davis | |
| 9,308,008 B2 | 4/2016 | Duncan et al. | |
| 9,364,201 B2 | 6/2016 | Orban, III | |
| 9,364,202 B2 | 6/2016 | Menn et al. | |
| 9,370,341 B2 | 6/2016 | Ceniccola et al. | |
| 9,370,378 B2 | 6/2016 | O'Prey et al. | |
| 9,375,224 B2 | 6/2016 | Jansen | |
| 9,414,817 B2 | 8/2016 | Taylor et al. | |
| 9,427,288 B1 | 8/2016 | Chenger et al. | |
| 9,468,452 B2 | 10/2016 | Menn et al. | |
| 9,486,188 B2 | 11/2016 | Secrest et al. | |
| 9,522,034 B2 | 12/2016 | Johnson et al. | |
| 9,549,747 B2 | 1/2017 | Carlson | |
| 9,579,115 B2 | 2/2017 | Kahle et al. | |
| 9,592,067 B2 | 3/2017 | Hartoumbekis | |
| 9,622,730 B2 | 4/2017 | Farascioni | |
| 9,629,618 B2 | 4/2017 | Davis et al. | |
| 9,642,638 B1 | 5/2017 | Carrier | |
| 9,655,644 B2 | 5/2017 | Collins | |
| 9,730,716 B2 | 8/2017 | Secrest et al. | |
| 9,789,268 B2 | 10/2017 | Hart et al. | |
| 9,808,228 B2 | 11/2017 | Kondrup et al. | |
| 9,826,997 B2 | 11/2017 | Cherry et al. | |
| 9,867,600 B2 | 1/2018 | Parihar et al. | |
| 9,877,893 B2 | 1/2018 | Taylor et al. | |
| 10,076,358 B2 | 9/2018 | Zergiebel et al. | |
| 2005/0054993 A1 | 3/2005 | Falahee | |
| 2008/0033344 A1 * | 2/2008 | Mantell ............. | A61M 39/0247 604/27 |
| 2008/0082084 A1 * | 4/2008 | Roberts ............. | A61M 1/0023 604/540 |
| 2011/0021879 A1 | 1/2011 | Hart et al. | |
| 2012/0089093 A1 | 4/2012 | Trusty | |
| 2012/0289785 A1 | 11/2012 | Albrecht et al. | |
| 2013/0204287 A1 | 8/2013 | Mark et al. | |
| 2017/0049474 A1 | 2/2017 | Piskun et al. | |
| 2017/0340866 A1 | 11/2017 | Richard | |

(56) References Cited

U.S. PATENT DOCUMENTS

2019/0110786 A1\* 4/2019 Ip .................. A61B 17/0218
2019/0142463 A1   5/2019 Zhu

\* cited by examiner

TISSUE GUARDS AND SYSTEMS INCORPORATING THE SAME FOR TISSUE SPECIMEN REMOVAL PROCEDURES AND OTHER SURGICAL PROCEDURES

CROSS-REFERENCE TO RELATED APPLICATIONS

This application claims the benefit of, and priority to, U.S. Provisional Patent Application No. 62/852,223, filed on May 23, 2019, the entire contents of which are hereby incorporated herein by reference.

FIELD

The present disclosure relates to tissue specimen removal and, more particularly, to tissue guards and systems incorporating the same for use in tissue specimen removal procedures and other surgical procedures.

BACKGROUND

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a tissue guard including a body and a lip. The body defines an open proximal end, an open distal end, and a lumen extending through the body between the open proximal end and the open distal end. The lip extends radially outwardly from the open proximal end of the body and includes a plurality of spaced-apart cut-outs defined about the outer circumference of the lip to define a plurality of tabs of the lip. Each tab includes an outer edge segment. The body and the lip are monolithically formed as a single piece of material.

In an aspect of the present disclosure, the lip is directly connected to the open proximal end of the body.

In another aspect of the present disclosure, a collar is disposed between and interconnects the open proximal end of the body and the lip. The collar is monolithically formed as part of the single piece of material with the body and the lip.

In still another aspect of the present disclosure, the collar includes an outwardly-facing channel extending about an outer circumference of the collar, a plurality of slots spaced-apart about an inner circumference of the collar and defined through the collar in fluid communication with the channel, and a connection port disposed in fluid communication with the channel.

In yet another aspect of the present disclosure, the collar is configured to interface with tissue or an access device to seal the channel, thereby defining a sealed channel.

In still yet another aspect of the present disclosure, the tissue guard further includes a plurality of longitudinally-extending spines formed on an exterior surface of at least one of the body or the lip and/or a plurality of radially-extending spines formed on an exterior surface of at least one of the body or the lip.

A system provided in accordance with aspects of the present disclosure includes an access device and a tissue guard. The access device includes a proximal end portion, a distal end portion, and a body extending between the proximal and distal end portions. The body defines a passageway extending therethrough. The proximal end portion defines an overhang extending radially-inwardly into the passageway. The tissue guard includes a body defining an open proximal end, an open distal end, and a lumen extending through the body between the open proximal end and the open distal end. The tissue guard further includes a lip extending radially outwardly from the open proximal end of the body. The lip includes a plurality of spaced-apart cut-outs defined about the outer circumference of the lip to define a plurality of tabs of the lip. Each tab includes an outer edge segment. The outer edge segments of the lip are configured to engage the overhang to thereby engage the tissue guard within the access device.

In an aspect of the present disclosure, the access device is a tissue retractor. In such aspects, the proximal end portion may be a proximal rim, the distal end portion may be a distal rim, and the tissue retractor may be selectively adjustable by rolling the proximal rim distally about the body.

In another aspect of the present disclosure, an outer diameter of the lip of the tissue guard is greater than an inner diameter of the proximal end portion of the access device such that the lip of the tissue guard is required to be flexed to pass distally through the proximal end portion of the access device.

In still another aspect of the present disclosure, the body and the lip of the tissue guard are monolithically formed as a single piece of material.

In still yet another aspect of the present disclosure, with the tissue guard engaged within the access device, a longitudinal axis of the tissue guard and a longitudinal axis of the access device are coaxial.

In another aspect of the present disclosure, the tissue guard is configured to snap into engagement within the access device, thereby providing at least one of audible or tactile confirmation of the engagement therebetween.

In yet another aspect of the present disclosure, the tissue guard further includes a plurality of longitudinally-extending spines formed on an exterior surface of at least one of the body or the lip and/or a plurality of radially-extending spines formed on the exterior surface of at least one of the body or the lip.

Another system provided in accordance with aspects of the present disclosure includes a tissue guard and first tubing. The tissue guard includes a body defining an open proximal end, an open distal end, and a lumen extending through the body between the open proximal end and the open distal end. A lip extends radially outwardly from the open proximal end of the body, and a collar is disposed between and interconnecting the open proximal end of the body and the lip. The collar includes an outwardly-facing channel extending about an outer circumference of the collar, a plurality of slots spaced-apart about an inner circumference of the collar through the collar in fluid communication with the channel, and a connection port disposed in fluid communication with the channel. The first tubing is configured to couple to the connection port at a first end of the first tubing.

In an aspect of the present disclosure, the system further includes a smoke evacuation source. A second end of the first tubing is configured to couple (directly or indirectly) to the smoke evacuation source.

In another aspect of the present disclosure, the system further includes a collection reservoir and second tubing. In such aspects, the second end of the first tubing is configured to connect to the collection reservoir and the second tubing is configured to connect between the collection reservoir and the smoke evacuation source to thereby couple the second end of the first tubing with the smoke evacuation source.

In still another aspect of the present disclosure, the collar of the tissue guard is configured to interface with tissue or an access device to seal the channel, thereby defining a sealed channel.

In yet another aspect of the present disclosure, the system further includes an access device. In such aspects, the tissue guard is configured for releasable engagement within the access device.

In still yet another aspect of the present disclosure, the lip of the tissue guard includes a plurality of spaced-apart cut-outs defined about the outer circumference of the lip to define a plurality of tabs of the lip. Each tab includes an outer edge segment.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1A:
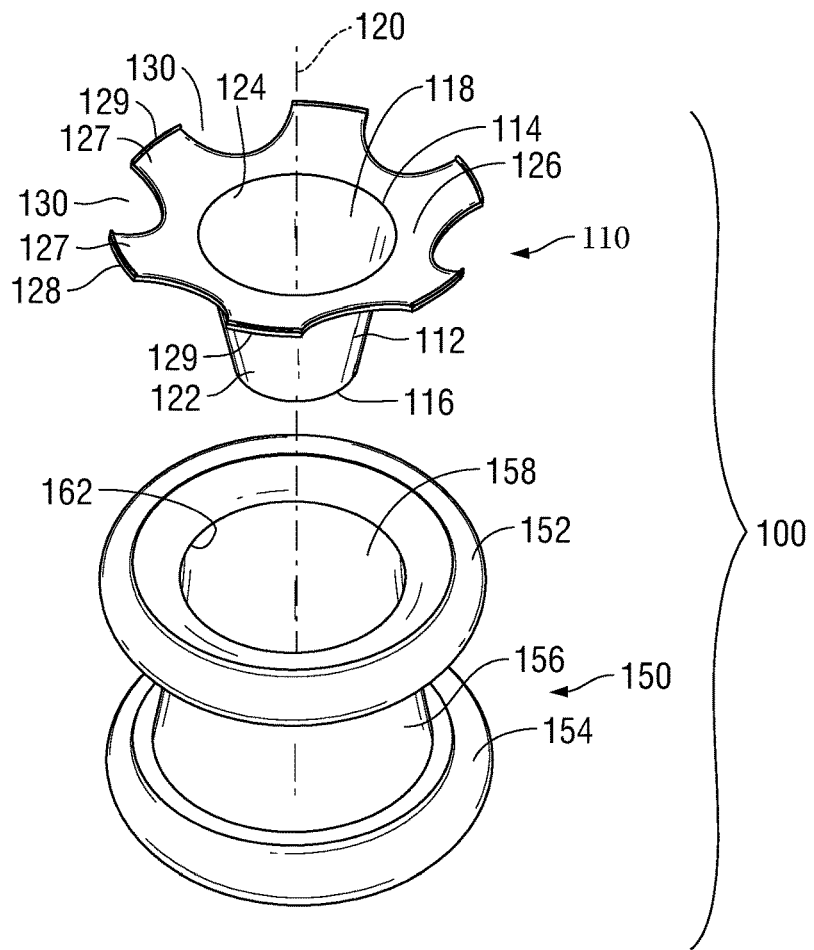
FIG. 1A is an exploded, top, perspective view of a system provided in accordance with the present disclosure including an access device and a tissue guard.
Figure 1B:
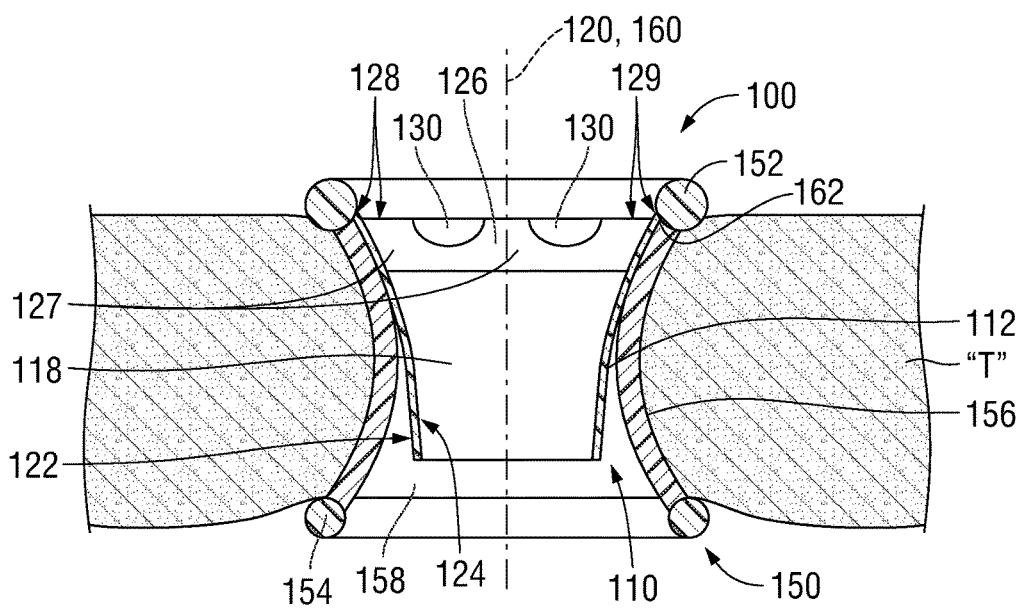
FIG. 1B is a cross-sectional view of the system of FIG. 1A disposed within an opening in tissue.

Turning to FIGS. 1A and 1B, a system 100 provided in accordance with the present disclosure includes a tissue guard 110 and an access device 150. Tissue guard 110 is monolithically formed as a single piece of material, e.g., a biocompatible plastic such as, for example, polyethylene, polycarbonate, etc., from any suitable method, e.g., injection molding. The material, thickness, and configuration of tissue guard 110 are such that tissue guard 110 defines sufficient stiffness to maintain its shape when positioned within an opening in tissue "T" and/or when engaged within access device 150. However, the material, thickness, and configuration of tissue guard 110 also provide sufficient resilient flexibility to permit manipulation of tissue guard 110 from an at-rest position for insertion into an opening in tissue "T" and/or for engagement within access device 150, with tissue guard 110 returning to or towards the at-rest position after insertion and/or engagement. Further, the material, thickness, and configuration of tissue guard 110 is selected such that tissue guard 110 is configured to withstand cutting and puncturing by surgical knives, scalpels, pencils, and the like, thereby protecting surrounding tissue "T" and/or access device 150 from being cut or punctured. Tissue guard 110 may additionally or alternatively be configured to inhibit transfer of thermal and/or electrical energy therethrough to protect surrounding tissue "T" and/or access device 150 from thermal and/or electrical energy.

Continuing with reference to FIGS. 1A and 1B, tissue guard 110 includes a body 112 defining an open proximal end 114, an open distal end 116, and a lumen 118 extending therethrough between open proximal and distal ends 114, 116, respectively. Lumen 118 defines a longitudinal axis 120 and is configured to receive one or more surgical instruments (not shown) therethrough. In embodiments, body 112 defines a funnel-shaped configuration wherein a diameter of body 112 at open proximal end 114 thereof is greater than a diameter of body 112 at open distal end 116 thereof. Additionally or alternatively, the exterior surface 122 of body 112 defines a concave configuration while the interior surface 124 of body 112, which defines lumen 118, defines a convex configuration.

Tissue guard 110 further includes a lip 126 extending radially outwardly from open proximal end 114 of body 112 about the annular perimeter thereof. In this manner, lip 126 extends radially outwardly from lumen 118. Lip 126 may extend radially outwardly from body 112 at an oblique angle relative thereto. More specifically, an angle defined between lip 126 and the exterior surface 122 of body 112 may, in embodiments, be from about 90 degrees to about 135 degrees. Lip 126 defines a circumferential outer edge 128. A plurality of spaced-apart cut-outs 130 are defined about the outer circumference of lip 126, thereby interrupting outer edge 128 of lip 126 such that lip 126 defines a plurality of spaced-apart tabs 127 each including an outer edge segment 129 of discontinuous outer edge 128. Cut-outs 130 facilitate flexion of lip 126, e.g., to facilitate insertion into an opening in tissue "T" and/or engagement within access device 150.

Referring still to FIGS. 1A and 1B, access device 150 may be configured as a tissue retractor, an access port, or other suitable access device configured for positioning within an opening in tissue "T," e.g., a surgical incision or a naturally-occurring orifice, to provide access therethrough into an internal surgical site. Access device 150 includes a proximal rim 152 configured for positioning on an external side of the opening in tissue "T," a distal rim 154 configured for positioning on an internal side of the opening in tissue "T,"

and a body 156 extending between proximal and distal rims 152, 154, respectively. Body 156 is configured to extend through the opening in tissue "T" and defines a passageway 158 extending longitudinally therethrough to permit access to an internal surgical site through the opening in tissue "T." Passageway 158 defines a longitudinal axis 160. At least a portion of body 156 of access device 150 may be flexible to facilitate insertion and positioning of access device 150 within the opening in tissue "T." In embodiments, body 156 is formed from a flexible sleeve of material including one or more layers of material. Further, access device 150 may be selectively adjustable, e.g., by rolling proximal rim 154 distally about body 156, to retract tissue "T" and/or secure access device 150 within the opening in tissue "T." Access device 150 further defines an inwardly-extending overhang 162 between proximal rim 154 and body 156 and extending annularly about passageway 158.

As shown in FIG. 1B, in use, access device 150 is positioned within an opening in tissue "T" such that, as noted above, distal rim 154 is disposed on an internal surface of tissue "T" on the internal side of the opening in tissue "T," body 156 extends through the opening in tissue "T," and proximal rim 152 is disposed on an exterior surface of tissue "T" on the external side of the opening in tissue "T." As also noted above, access device 150 may be adjusted to conform access device 150 to a patient's anatomy, retracting tissue "T" and/or securing access device 150 within the opening in tissue "T."

With access device 150 disposed within the opening in tissue "T," tissue guard 110, lead by open distal end 116 thereof, is inserted into passageway 158. Tissue guard 110 is configured relative to access device 150 such that an outer diameter of outer edge 128 of lip 126 of tissue guard 110 is greater than an inner diameter of proximal rim 152 of access device 150 such that tissue guard 110 is required to be flexed or otherwise manipulated to permit lip 126 to pass distally through proximal rim 152 into the portion of passageway 158 defined by body 156 of access device 150. More specifically, tissue guard 110 may be flexed or otherwise manipulated such that tabs 127 of lip 126 are urged proximally and inwardly relative to body 112, thus reducing the outer-most diameter of tissue guard 110 to facilitate passage through proximal rim 152 of access device 150. Cut-outs 130, as noted above, facilitate the flexion of lip 126 in this manner to enable passage through proximal rim 152 of access device 150.

Once tissue guard 110 is inserted sufficiently into passageway 158 of access device 150 such that lip 126 is disposed distally of proximal rim 152 of access device 150, tissue guard 110 may be released, allowing tissue guard 110 to return to or towards its at-rest position, whereby tabs 127 of lip 126 and, more specifically, outer edge segments 129 of tabs 127, are engaged with overhang 162, thereby locking tissue guard 110 in engagement within access device 150. In embodiments, tabs 127 of lip 126 may be configured to "snap" into engagement with overhang 162 and, in such embodiments, may produce an audible and/or tactile response that confirms the engagement of tissue guard 110 within access device 150.

With tissue guard 110 engaged within access device 150 as detailed above, surgical instrumentation may be inserted through lumen 118 of tissue guard 110 into the internal surgical site to, for example, extract a tissue specimen therefrom. Tissue guard 110, as noted above, protects tissue "T" as well as access device 150 during the insertion, manipulation, use and withdrawal of any such surgical instrumentation.

Figure 2:
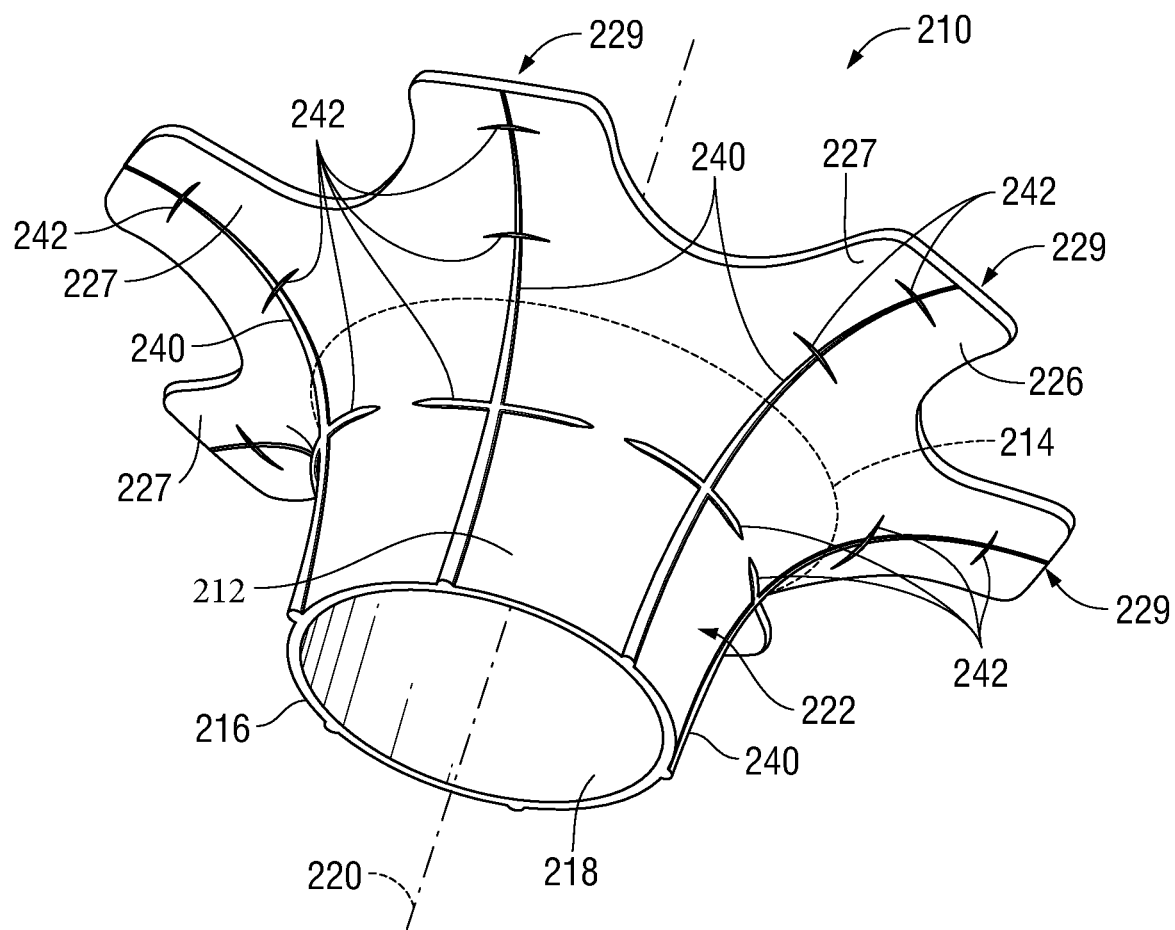
FIG. 2 is a bottom, perspective view of another tissue guard provided in accordance with the present disclosure.

Turning to FIG. 2, another tissue guard 210 provided in accordance with the present disclosure is shown. With additional momentary reference to FIG. 1A, tissue guard 210 is similar to tissue guard 110 except as explicitly contradicted below and may be used in conjunction with access device 150 as part of a system similar to system 100. For purposes of brevity, only differences between tissue guard 210 and tissue guard 110 are detailed below, while similarities are summarily described or omitted.

Tissue guard 210 includes a body 212 defining an open proximal end 214, an open distal end 216, and a lumen 218. Lumen 218 defines a longitudinal axis 220. A lip 226 including a plurality of spaced-apart tabs 227 extends radially outwardly from open proximal end 214 of body 212.

Tissue guard 210 further includes a plurality of longitudinally-extending spines 240 formed on exterior surface 222 of tissue guard 210 and spaced-apart annularly about tissue guard 210. Longitudinally-extending spines 240 extend along a portion of the length of tissue guard 210 including at least a majority of the length of body 212 and/or at least a majority of the length of lip 226. In embodiments, longitudinally-extending spines 240 extend the length of tissue guard 210 from the open distal end 216 thereof to the outer edge segments 229 of tabs 227. Further, longitudinally-extending spines 240 may taper in height and/or width in a distal to proximal direction. In embodiments, longitudinally-extending spines 240 define semi-circular cross-sectional configurations wherein the radii thereof taper in a distal to proximal direction. Longitudinally-extending spines 240, in embodiments, may be equally-spaced relative to one another with each longitudinally-extending spine 240 centered on one of the tabs 227 of lip 226. Longitudinally-extending spines 240 are configured to selectively provide additional structural support to tissue guard 210, e.g., providing greater structure support in one or more direction as compared to one or more other directions.

Continuing with reference to FIG. 2, tissue guard 210 additionally includes a plurality of radially-extending spines 242 associated with each longitudinally-extending spine 240. Radially-extending spines 242 are formed on exterior surface 222 of tissue guard 210 and extend from either side of the corresponding longitudinally-extending spine 240 radially about a portion of the periphery of tissue guard 210. At least a first set of radially-extending spines 242 may be disposed on body portion 212 of tissue guard 210, and at least a second set of radially-extending spines 242 may be disposed on lip 226 of tissue guard 210, e.g., with each tab 227 including one or more radially-extending spines 242. Radially-extending spines 242 may extend perpendicularly relative to longitudinally-extending spines 240 or may be disposed at an oblique angle relative thereto. In embodiments, more-distal radially-extending spines 242 defines greater lengths and/or thicknesses as compared to more-proximal radially-extending spines 242. Radially-extending spines 242 provide secondary support to tissue guard 210 and help distribute forces about tissue guard 210 during flexion thereof.

The above-detailed configuration of spines 240, 242 provides increased structural support to tissue guard 210 in some directions of force while maintaining flexibility in other directions of force. More specifically, spines 240, 242 maintain flexibility of tabs 227 of lip 226 from the at-rest position proximally and inwardly relative to body 212, thus enabling flexion of tissue guard 210 for insertion, as detailed above with respect to tissue guard 110 (FIGS. 1A and 1B). However, spines 240, 242 provide increased structural support to tissue guard 210 with respect to flexion of tabs 227 of lip 226 from the at-rest position distally and outwardly relative to body 212, thus helping to maintain tissue guard 210 in position and in engagement during use.

Figure 3A:
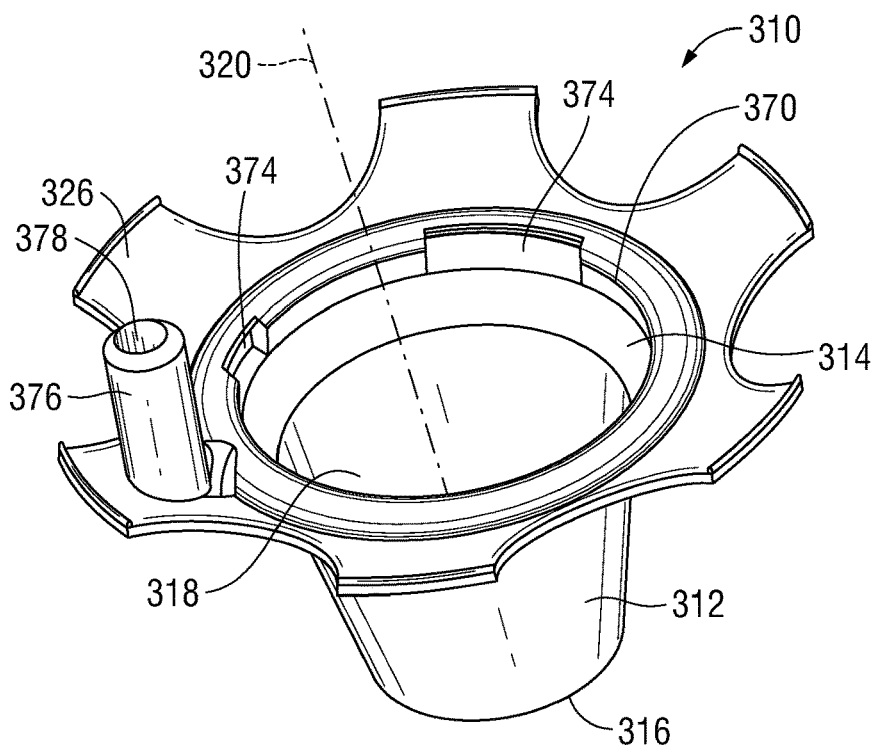
FIGS. 3A and 3B are respective top and bottom perspective views of another tissue guard provided in accordance with the present disclosure.
Figure 3B:
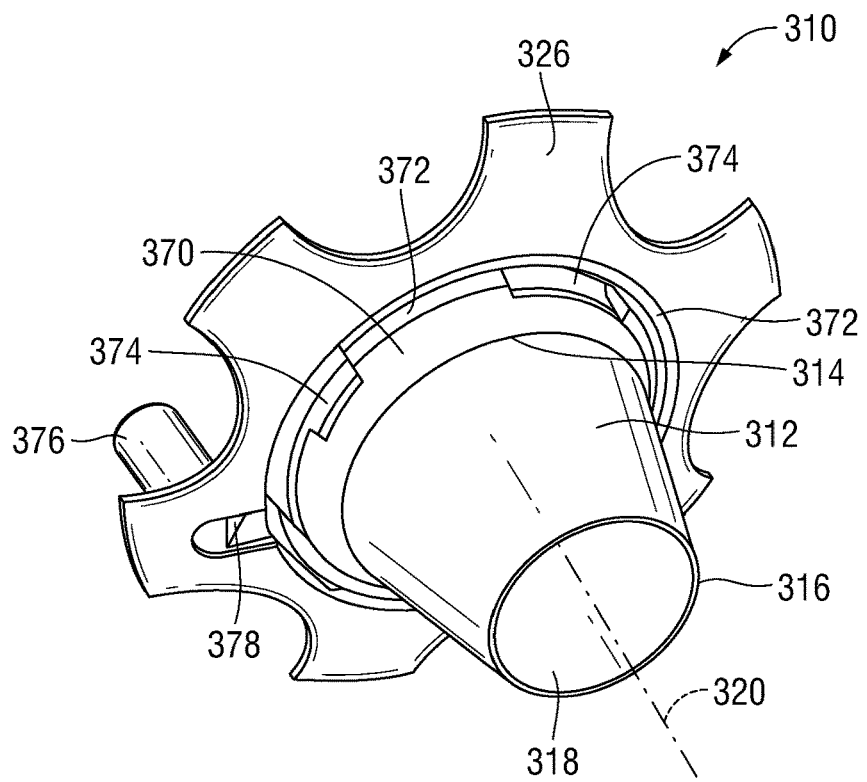
Figure 3C:
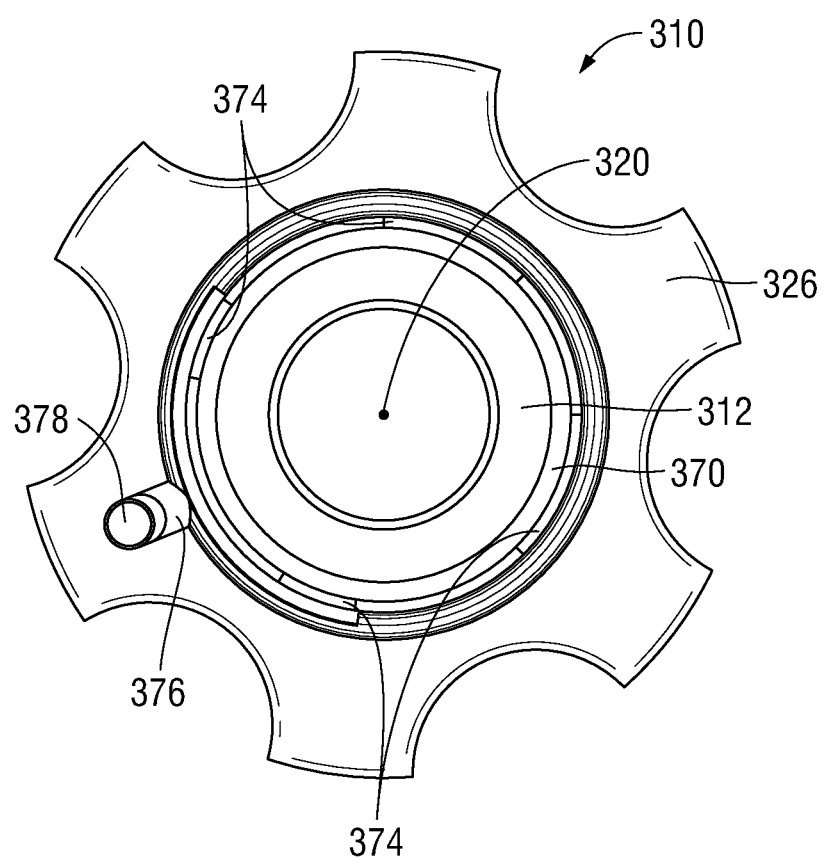
FIG. 3C is a top view of the tissue guard of FIGS. 3A and 3B.

Referring to FIGS. 3A-3C, another tissue guard 310 provided in accordance with the present disclosure is shown. With additional momentary reference to FIGS. 1A and 2, tissue guard 310 is similar to tissue guards 110, 210 and may include any of the features thereof, except as explicitly contradicted below. Further, tissue guard 310 may be used in conjunction with access device 150 as part of a system similar to system 100. Alternatively, tissue guard 310 may be utilized as a stand-alone device, as detailed below. Tissue guards 110, 210 may likewise be used as stand-alone devices, similarly as detailed below with respect to tissue guard 310. For purposes of brevity, only differences between tissue guard 310 and tissue guards 110, 210 are detailed below, while similarities are summarily described or omitted.

Tissue guard 310 includes a body 312 defining an open proximal end 314, an open distal end 316, and a lumen 318 extending therethrough and defining a longitudinal axis 320. Tissue guard 110 further includes a collar 370 disposed about open proximal end 314 of body 312 and a lip 326 extending radially outwardly from collar 370. Thus, as opposed to tissue guard 110, wherein lip 126 directly extends radially outwardly from open proximal end 114 of body 112 (see FIGS. 1A and 1B), tissue guard 310 includes collar 370 interdisposed between and interconnecting open proximal end 314 of body 312 and lip 326.

Continuing with reference to FIGS. 3A-3C, collar 370 defines a channel 372 on an outwardly-facing side thereof. Channel 372 extends annularly about the outer circumference of collar 370 and is disposed between open proximal end 314 of body 312 and lip 326. Channel 372 may define a semi-circular cross-sectional configuration or any other suitable cross-sectional configuration. Collar 370 further includes a plurality of slots 374 spaced-apart about the circumference thereof. Slots 374 are defined fully through collar 370 to establish fluid communication between channel 372, disposed on the outwardly-facing side of tissue guard 310, and lumen 318, disposed on the inwardly-facing side of tissue guard 310, at a plurality of radial positions about tissue guard 310.

Collar 370 additionally includes a connection port 376 extending proximally from lip 326. Connection port 376 defines a port lumen 378 therethrough that is disposed in fluid communication with channel 372 (see FIG. 5). Connection port 376 is configured to enable connection of suitable tubing 710 (see FIG. 4) thereto to thereby define a flow path from channel 372, through port lumen 378, to the tubing 710 (see FIG. 4).

Figure 4:
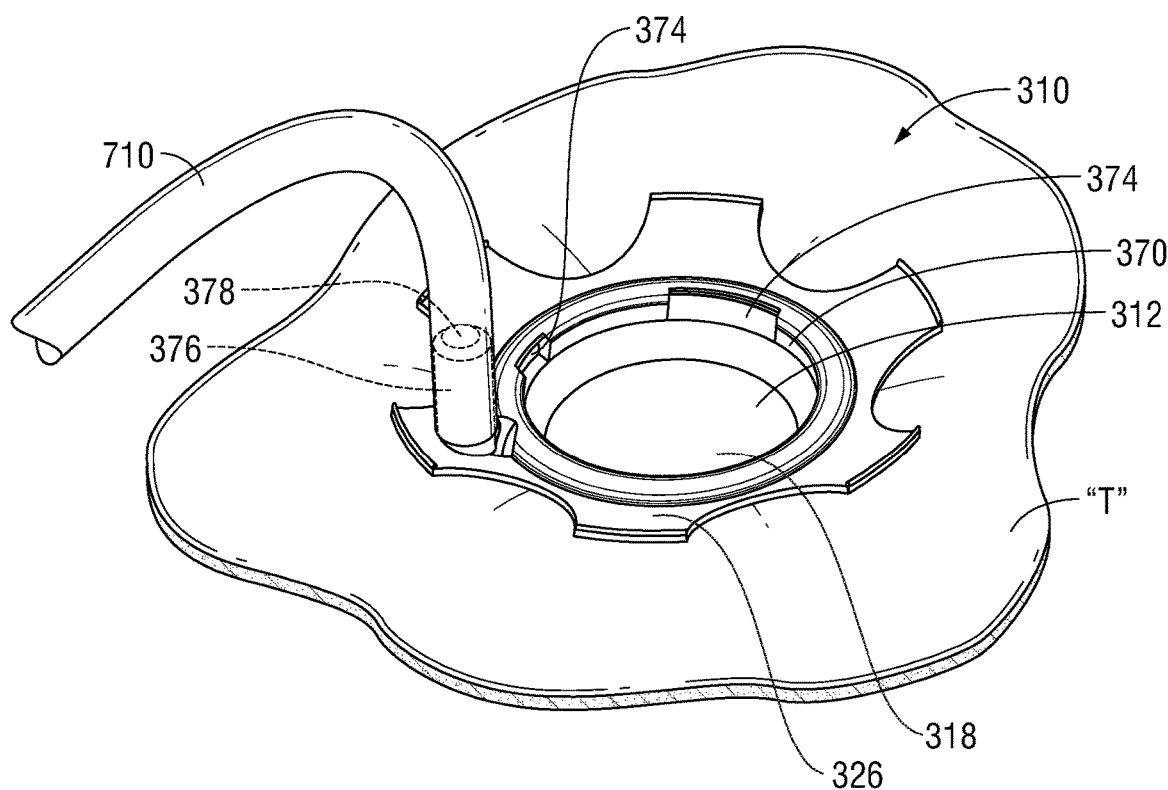
FIG. 4 is a top, perspective view of the tissue guard of FIGS. 3A and 3B disposed within an opening in tissue and including tubing coupled thereto.
Figure 5:
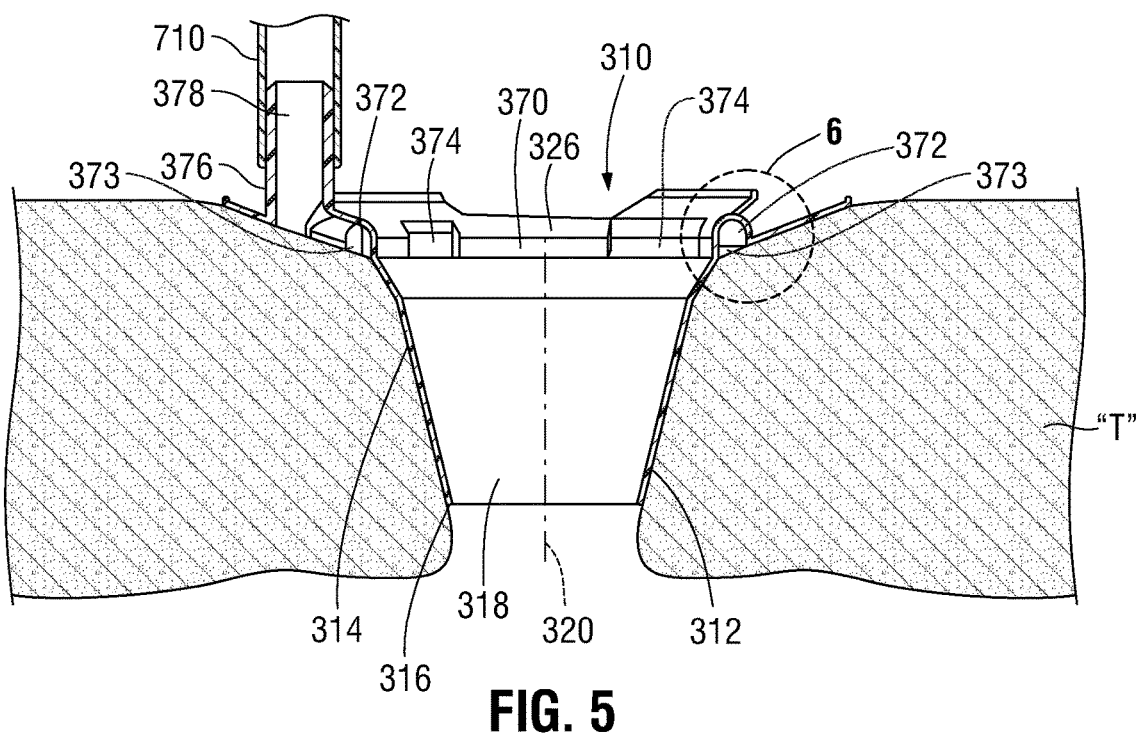
FIG. 5 is a cross-sectional view of the tissue guard of FIGS. 3A and 3B disposed within an opening in tissue and including tubing coupled thereto.
Figure 6:
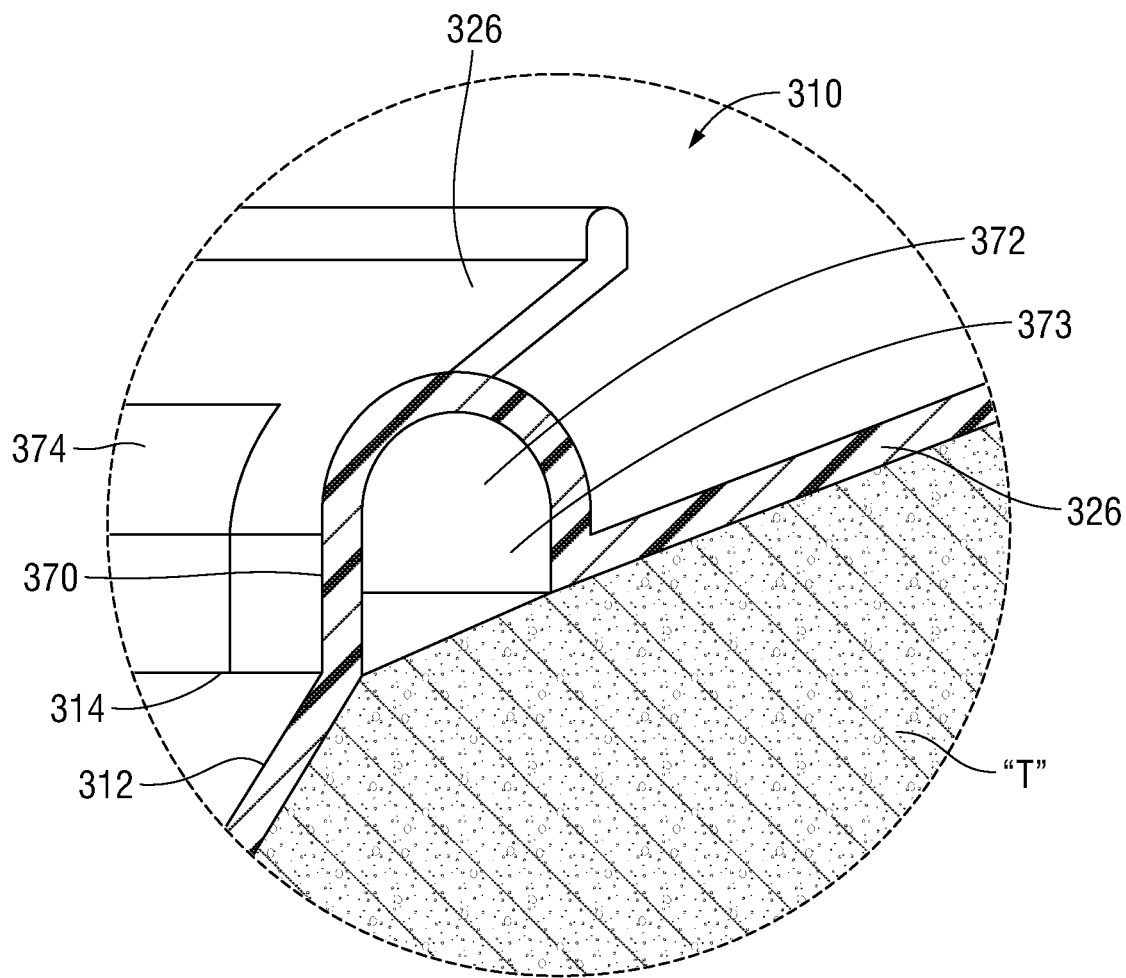
FIG. 6 is an enlarged, cross-sectional view of the area of detail indicated as "6" in FIG. 5.

With additional reference to FIGS. 4-6, tissue guard 310 is shown in use engaged within an opening in tissue "T." More specifically, tissue guard 310 is positioned with body 312 extending at least partially through the opening in tissue "T," while lip 326 extends radially outwardly from the opening in tissue "T" about the external surface of tissue "T." Depending upon the size of the opening in tissue "T," body 312 may press against and/or retract tissue "T" surrounding the opening in tissue "T" to maintain and/or enlarge the opening in tissue "T." With body 312 pressing against and/or retracting tissue "T," collar 370 is urged into sealing engagement with tissue "T" such that the inner surface of tissue "T" surrounding the opening in tissue "T" cooperates with channel 372 to define a sealed lumen 373 extending radially about tissue guard 310 between tissue guard 310 and tissue "T" (see FIG. 6). In embodiments where tissue guard 310 is used in conjunction with an access device, e.g., access device 150 (FIGS. 1A and 1B), tissue guard 310 is engaged within the access device whereby collar 370 is urged into sealing engagement with the inwardly-facing surface of the body of the access device such that the inwardly-facing surface of the body of the access device cooperates with channel 372 to define the sealed lumen 373.

Continuing with reference to FIGS. 4-6, slots 374 of collar 370 of tissue guard 310, sealed lumen 373 formed via channel 372 and tissue "T," and port lumen 378 of connection port 376 cooperate to define a flow path from lumen 318 of tissue guard 310 to tubing 710. Tissue guard 310 and tubing 710 may be part of an outflow system, e.g., a smoke evacuation system 700 (FIG. 7), or may be part of an inflow system, e.g., an aspiration system (not shown). With respect to either an outflow system or an inflow system, the positioning of slots 374 radially-spaced about lumen 318 of tissue guard 310 provides outflow or inflow at a plurality of positions radially-spaced about lumen 318 of tissue guard 310, thus facilitating outflow or inflow and more uniform distribution thereof.

Figure 7:
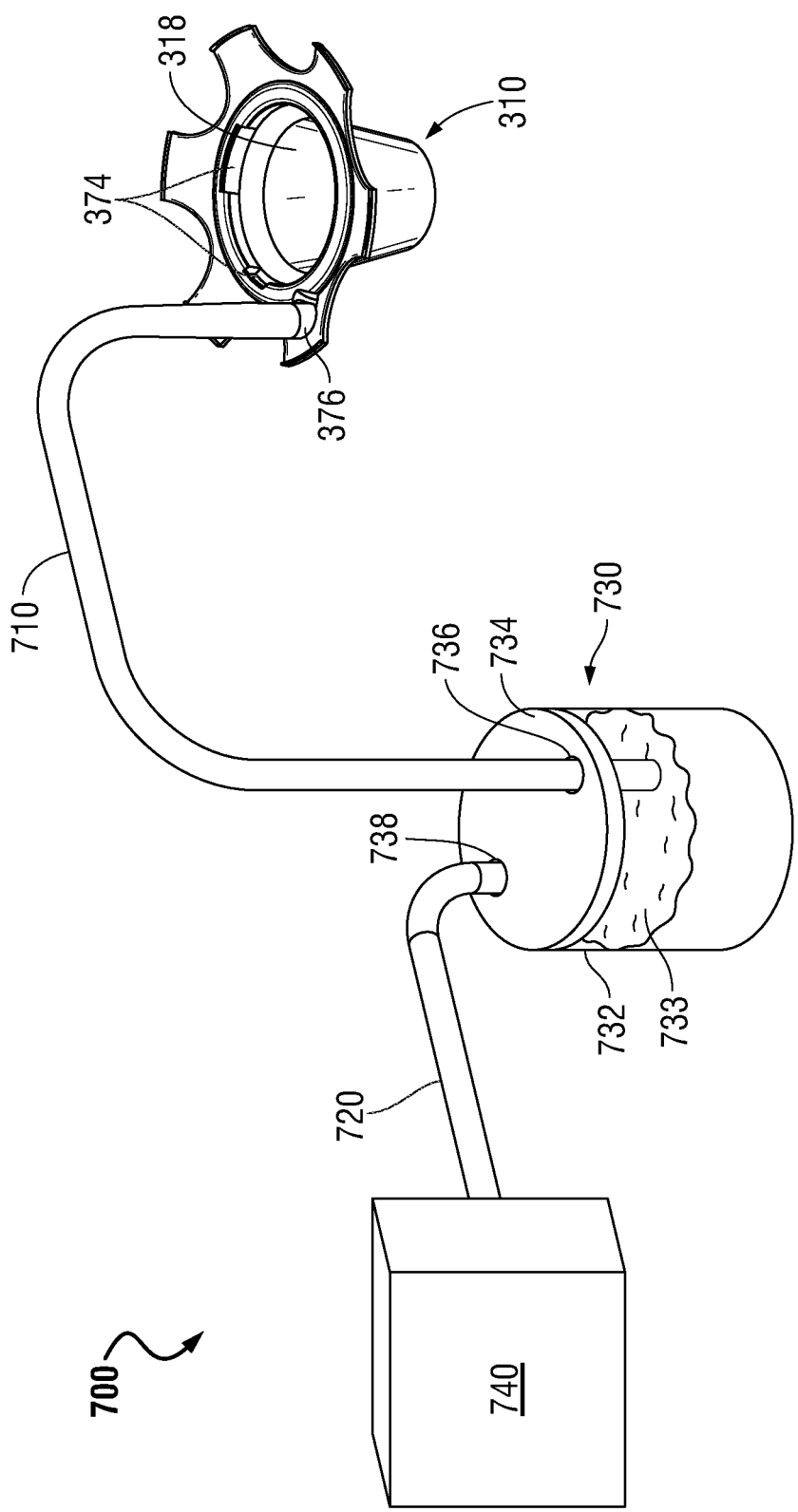
FIG. 7 is a system provided in accordance with the present disclosure including the tissue guard of FIGS. 3A and 3B, tubing, a collection reservoir, and a smoke evacuation source.

Turning to FIG. 7, a smoke evacuation system 700 provided in accordance with the present disclosure is shown generally including tissue guard 310, tubing 710, 720, a collection reservoir 730, and a smoke evacuation (or vacuum) source 740. Tissue guard 310 and tubing 710 are detailed above and are coupled to one another, e.g., via engagement of one end of tubing 710 about connection port 376 of tissue guard 310. The other end of tubing 710 extends into collection reservoir 730 in sealing relation therewith.

Collection reservoir 730 includes a base 732 and a lid 734 sealed about base 732. Lid 734 defines first and second ports 736, 738 configured to receive ends of tubing 710, 720, respectively, in sealing relation therewith. These ends of tubing 710, 720 extend into the interior volume 733 of base 732 and are spaced-apart from one another as well as the bottom of base 732. Tubing 720 extends from collection reservoir 730 to smoke evacuation source 740 wherein the other end of tubing 720 is coupled to smoke evacuation source 740. In this manner, upon activation of smoke evacuation source 740, suction is established through slots 374 of tissue guard 310, tubing 710, collection reservoir 730, tubing 720, to smoke evacuation source 740. During use, this suction, in addition to evacuating smoke from lumen 318 of tissue guard 310, may also suction liquids, tissue, and/or debris through tubing 710. However, as a result of the ends of tubing 710, 720 being spaced-apart from one another within collection reservoir 730 and spaced-apart from the bottom of base 732 of collection reservoir 730, the liquids, tissue, and/or debris are suctioned into collection reservoir 730 and deposited therein, while only the smoke and other gaseous fluids are further suctioned from collection reservoir 730 through tubing 720 to smoke evacuation source 740. As such, smoke evacuation source 740 is protected by inhibiting suctioning of liquids, tissue, and/or debris into smoke evacuation source 740.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue guard, comprising:
   a body defining an open proximal end, an open distal end, and a lumen extending through the body between the open proximal end and the open distal end;
   a lip extending radially outwardly from the open proximal end of the body, the lip including a plurality of spaced-apart cut-outs defined about the outer circumference of the lip to define a plurality of tabs of the lip, each tab including an outer edge segment, wherein the body and the lip are monolithically formed as a single piece of material; and
   a collar disposed between and interconnecting the open proximal end of the body and the lip, the collar monolithically formed as part of the single piece of material with the body and the lip, wherein the collar includes:
      an outwardly-facing channel extending about an outer circumference of the collar;
      a plurality of slots spaced-apart about an inner circumference of the collar, the slots defined through the collar and disposed in fluid communication with the channel; and
      a connection port disposed in fluid communication with the channel.

2. The tissue guard according to claim 1, wherein the lip is directly connected to the open proximal end of the body.

3. The tissue guard according to claim 1, wherein the collar is configured to interface with tissue or an access device to seal the channel, thereby defining a sealed channel.

4. The tissue guard according to claim 1, further comprising a plurality of longitudinally-extending spines formed on an exterior surface of at least one of the body or the lip.

5. The tissue guard according to claim 1, further comprising a plurality of radially-extending spines formed on an exterior surface of at least one of the body or the lip.

6. A system, comprising:
   an access device including a proximal end portion, a distal end portion, and a body extending between the proximal and distal end portions, the body defining a passageway extending therethrough, wherein the proximal end portion defines an overhang extending radially-inwardly into the passageway; and
   a tissue guard, including:
      a body defining an open proximal end, an open distal end, and a lumen extending through the body between the open proximal end and the open distal end; and
      a lip extending radially outwardly from the open proximal end of the body, the lip including a plurality of spaced-apart cut-outs defined about the outer circumference of the lip to define a plurality of tabs of the lip, each tab including an outer edge segment,
   wherein the outer edge segments of the lip are configured to engage the overhang to thereby engage the tissue guard within the access device.

7. The system according to claim 6, wherein the access device is a tissue retractor, the proximal end portion is a proximal rim, the distal end portion is a distal rim, and the tissue retractor is selectively adjustable by rolling the proximal rim distally about the body.

8. The system according to claim 6, wherein an outer diameter of the lip of the tissue guard is greater than an inner diameter of the proximal end portion of the access device such that the lip of the tissue guard is required to be flexed to pass distally through the proximal end portion of the access device.

9. The system according to claim 6, wherein the body and the lip of the tissue guard are monolithically formed as a single piece of material.

10. The system according to claim 6, wherein, with the tissue guard engaged within the access device, a longitudinal axis of the tissue guard and a longitudinal axis of the access device are coaxial.

11. The system according to claim 6, wherein the tissue guard is configured to snap into engagement within the access device, thereby providing at least one of audible or tactile confirmation of the engagement therebetween.

12. The system according to claim 6, wherein the tissue guard further includes at least one of:
   a plurality of longitudinally-extending spines formed on an exterior surface of at least one of the body or the lip; or
   a plurality of radially-extending spines formed on the exterior surface of at least one of the body or the lip.

13. A system, comprising:
   a tissue guard, including:
      a body defining an open proximal end, an open distal end, and a lumen extending through the body between the open proximal end and the open distal end;
      a lip extending radially outwardly from the open proximal end of the body; and
      a collar disposed between and interconnecting the open proximal end of the body and the lip, the collar including:
         an outwardly-facing channel extending about an outer circumference of the collar;
         a plurality of slots spaced-apart about an inner circumference of the collar, the slots defined through the collar and disposed in fluid communication with the channel; and
         a connection port disposed in fluid communication with the channel; and
   first tubing configured to couple to the connection port at a first end of the first tubing.

14. The system according to claim 13, further comprising a smoke evacuation source, wherein a second end of the first tubing is configured to couple to the smoke evacuation source.

15. The system according to claim 14, further comprising:
   a collection reservoir; and
   second tubing, wherein the second end of the first tubing is configured to connect to the collection reservoir and wherein the second tubing is configured to connect between the collection reservoir and the smoke evacuation source to thereby couple the second end of the first tubing with the smoke evacuation source.

16. The system according to claim 13, wherein the collar of the tissue guard is configured to interface with tissue or an access device to seal the channel, thereby defining a sealed channel.

17. The system according to claim 13, further comprising:
   an access device, wherein the tissue guard is configured for releasable engagement within the access device.

18. The system according to claim 13, wherein the lip of the tissue guard includes a plurality of spaced-apart cut-outs defined about the outer circumference of the lip to define a plurality of tabs of the lip, each tab including an outer edge segment.

* * * * *